United States Patent
Athwale et al.

(10) Patent No.: US 11,605,454 B2
(45) Date of Patent: Mar. 14, 2023

(54) METHOD AND SYSTEM FOR CACHING MEDICAL IMAGES BASED ON EXAMINATION PRIORITY

(71) Applicant: GE Precision Healthcare LLC, Wauwatosa, WI (US)

(72) Inventors: Ritesh M. Athwale, Palatine, IL (US); Vijay Kumar Reddy Arlagadda, Hoffman Estates, IL (US); Mark J. Niggemann, Palatine, IL (US); Pravin K. Patel, Hoffman Estates, IL (US); Marc B. Stanis, Wheaton, IL (US); Pratheesh Kumar Kesava Pillai, Buffalo Grove, IL (US); Garrett Rogers, Channahon, IL (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 394 days.

(21) Appl. No.: 16/991,501

(22) Filed: Aug. 12, 2020

(65) Prior Publication Data
US 2022/0051784 A1 Feb. 17, 2022

(51) Int. Cl.
*G16H 30/20* (2018.01)
*G06N 20/00* (2019.01)
(Continued)

(52) U.S. Cl.
CPC ............. *G16H 30/20* (2018.01); *G06F 16/51* (2019.01); *G06N 3/08* (2013.01); *G06N 20/00* (2019.01);
(Continued)

(58) Field of Classification Search
CPC ........ G16H 30/20; G16H 30/40; G16H 40/20; G16H 30/00; G06N 20/00; G06N 3/08; H04L 69/22; G06F 16/51
See application file for complete search history.

(56) References Cited

U.S. PATENT DOCUMENTS 9,754,074 B1 * 9/2017 Reicher ................. G06Q 10/10
11,089,105 B1 * 8/2021 Karumbunathan ..... G06F 3/065
(Continued)

FOREIGN PATENT DOCUMENTS

CA         3051767 A1 *  2/2020  ............... G06T 1/20
WO   WO-2018149787 A1 *  8/2018  ........... G06K 9/4604

*Primary Examiner* — Asghar H Bilgrami (57) ABSTRACT

Systems and methods for expediting medical image retrieval based on examination priority are provided. A method includes receiving medical images and parsing the contents to determine medical image information. The method includes applying priority rules based on the medical image information. The priority rules specify an image storage location for storing the medical images. The image storage locations include workstation cache memory and drives of a local storage system having different image access speeds that are slower than an access speed of the workstation cache memory. The method includes storing the medical images at the specified image storage location as defined by the priority rules and retrieving the medical images from the specified image storage location in response to a request to view the medical images at a workstation. The method includes presenting the medical images retrieved from the specified image storage location at a display device of the workstation.

12 Claims, 2 Drawing Sheets

(51) Int. Cl.
  *H04L 69/22* (2022.01)
  *G16H 30/40* (2018.01)
  *G16H 40/20* (2018.01)
  *G06N 3/08* (2006.01)
  *G06F 16/51* (2019.01)
  *G16H 30/00* (2018.01)

(52) U.S. Cl.
  CPC ............ *G16H 30/40* (2018.01); *G16H 40/20* (2018.01); *H04L 69/22* (2013.01)

(56) References Cited

U.S. PATENT DOCUMENTS

| | | | |
|---|---|---|---|
| 11,275,509 B1* | 3/2022 | Colgrove | G06F 11/1076 |
| 2015/0106344 A1* | 4/2015 | Wagner | G06F 16/256 |
| | | | 707/758 |
| 2017/0039322 A1* | 2/2017 | Reicher | G06F 16/583 |
| 2021/0265041 A1* | 8/2021 | Narayanan | G06F 21/6218 |
| 2021/0360066 A1* | 11/2021 | Karumbunathan | H04L 67/146 |

* cited by examiner

METHOD AND SYSTEM FOR CACHING MEDICAL IMAGES BASED ON EXAMINATION PRIORITY

FIELD

Certain embodiments relate to caching medical images based on examination priority. More specifically, certain embodiments relate to a method and system for expediting medical image retrieval based on examination priority by applying examination priority rules to medical images received at a picture archiving and communication system (PACS) to store the medical images at a workstation cache or an appropriate storage drive type at a local storage system.

BACKGROUND

Various medical imaging techniques, such as ultrasound imaging, computed tomography (CT), magnetic resonance imaging (MRI), computed radiography, X-ray, positron emission tomography (PET), and the like, may be used to image anatomical structures, such as organs, soft tissues, and bone, in a human body. The medical imaging techniques may be configured to acquire medical images, such as CT images, MRI images, ultrasound images, X-ray images, fluoroscopy images, angiography images, mammography images, breast tomosynthesis images, PET images, single photon emission computed tomography (SPECT) images, endoscopy images, microscopy images, optical coherence tomography (OCT) images, and the like. The acquired medical images may be stored at a local storage system of a picture archiving and communication system (PACS) for retrieval and review at a workstation. However, medical images may not be readily available for review by a radiologist or cardiologist at busy times during the day, which may be problematic when a patient requires immediate attention, such as an emergency room patient or a patient in a trauma care unit.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for expediting medical image retrieval based on examination priority by applying examination priority rules to medical images received at a picture archiving and communication system (PACS) to store the medical images at a workstation cache or an appropriate storage drive type at a local storage system, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for caching medical images based on examination priority. Various embodiments have the technical effect of expediting medical image retrieval based on examination priority by applying examination priority rules to medical images received at a picture archiving and communication system (PACS) to store the medical images at a workstation cache or an appropriate storage drive type at a local storage system. Aspects of the present disclosure have the technical effect of dynamically updating priority rules using artificial intelligence to detect patterns of use and anticipate examination needs. Various embodiments have the technical effect of providing a smart image cache engine integrated with an artificial intelligence system, the smart image cache engine configured to enforce priority rules. Certain embodiments have the technical effect of performing image processing and storage or caching prior to retrieval for viewing and diagnosis.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

Figure 1:
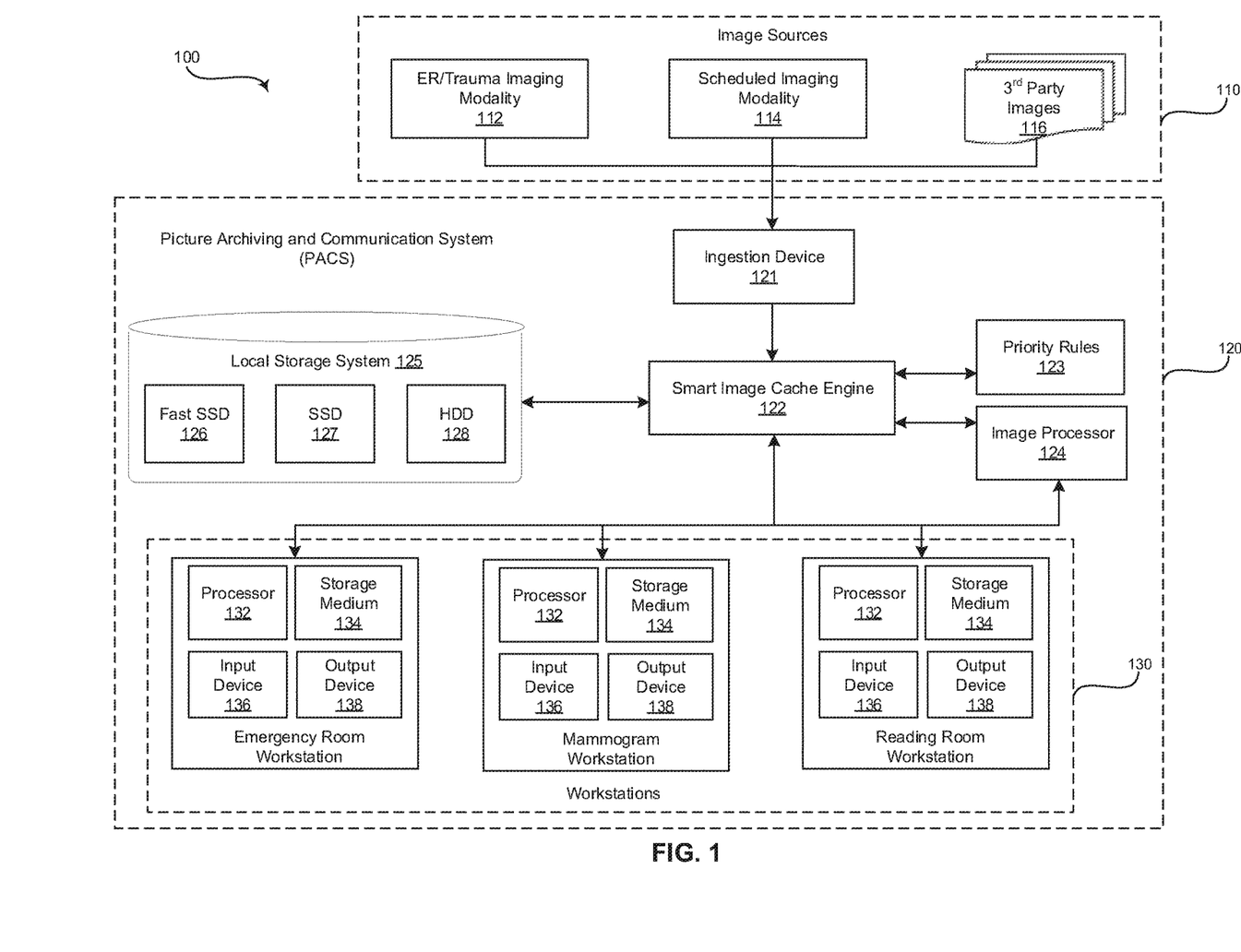
FIG. 1 is a block diagram of an exemplary medical imaging environment that is configured to expedite medical image retrieval based on examination priority, in accordance with various embodiments.

FIG. 1 is a block diagram of an exemplary medical imaging environment 100 that is configured to expedite medical image retrieval based on examination priority, in accordance with various embodiments. Referring to FIG. 1, there is shown a system 100 comprising one or more image sources 110 and a picture archiving and communication system (PACS) 120.

The image sources 110 may include imaging modalities 112, 114 at different locations within a medical imaging site, such as a hospital, and/or medical images from an external third party 116, such as a different hospital, doctor office, or the like. The different locations within a medical imaging site may include, for example, an emergency room and/or trauma unit 112 of the hospital, a medical imaging unit of a hospital used for scheduled or ordered examinations 114, a radiology unit, a cardiology unit, an obstetrics unit, and/or any suitable location at a medical imaging site. The imaging modalities may include ultrasound, computed tomography (CT), magnetic resonance imaging (MRI), computed radiography, X-ray, positron emission tomography (PET), and/or any suitable medical imaging modality. The medical images acquired by the imaging modalities 112, 114 and/or the third party images 116 may be DICOM files having a header and image data. The medical images may be provided from the image source(s) 110 to a PACS 120 that is communicatively coupled to the image source(s) 110.

The PACS 120 may comprise an ingestion device 121, a smart image cache engine 122, priority rules 123, an image processor 124, a local storage system 125, and one or more workstations 130. The ingestion device 121 may comprise suitable logic, circuitry, interfaces, and/or code configured to receive medical images from image sources 110. The ingestion device 121 may be configured to provide the received medical images to the smart image cache engine 122.

The smart image cache engine 122 may be one or more central processing units, microprocessors, microcontrollers, and/or the like. The smart image cache engine 122 may be an integrated component, or may be distributed across various locations, for example. The smart image cache engine 122 may be capable of receiving image retrieval and/or processing requests from workstation(s) 130, receiving medical images from ingestion device 121, local storage system 125, image processor 124, and/or workstation(s) 130, parsing the contents of the medical images, and routing the medical images to image processor 124, local storage system 125, and/or workstation cache memory 134, among other things. The smart image cache engine 122 may be capable of executing any of the method(s) and/or set(s) of instructions discussed herein in accordance with the various embodiments, for example.

The smart image cache engine 122 may comprise suitable logic, circuitry, interfaces, and/or code configured to automatically parse the contents of received medical images to determine medical image information. For example, the smart image cache engine 122 may be configured to determine an image source 110 location or type, such as images from an ER/Trauma imaging modality 112, images from a scheduled or ordered imaging examination 114, images from an external or third party source 116, and the like. As other examples, the smart image cache engine 122 may be configured to determine an imaging modality type (e.g., ultrasound, CT, MRI, CR, X-ray, PET, etc.), an image type (e.g., two-dimensional (2D), three-dimensional (3D), etc.), an examination procedure description (e.g., mammogram screening, diagnostic mammogram, head scan, chest scan, broken arm, etc.), and/or any suitable medical image information. The smart image cache engine 122 may retrieve priority rules 123 from any suitable data storage medium and apply the priority rules 123 to route the image data to an appropriate storage and/or processing location. For example, the priority rules 123 may prioritize images based on image source 110 locations, examination procedure types, image types, and/or any suitable image information or combination of information.

The priority rules 123 may be arranged in a look-up table (LUT) or as any suitable set of rules. The priority rules 123 may be user-defined and/or dynamically created, removed, and/or revised based on artificial intelligence detected patterns of user interactions with medical images. The priority rules 123 may prioritize certain image source 110 locations or types over other image source 110 locations or types. For example, the priority rules 123 may specify that medical images from an ER/Trauma imaging modality 112 (e.g., located at an emergency room or trauma center) are a highest priority that are provided to cache memory 134 (e.g., fastest option) of a particular ER workstation 130 to expedite retrieval and review of the medical images. The priority rules 123 may specify that medical images from an imaging modality corresponding with a scheduled or ordered imaging examination 114 (e.g., in-patient department, out-patient department, cardiology department, radiology department, etc.) have a second highest priority and are provided to a fast solid state drive (SSD) 126 (e.g., second fastest option) or SSD 127 (e.g., third fastest option) of a local storage system 125. The priority rules 123 may specify that third party medical images 116 from an external source (e.g., other hospital or doctor office) are associated with a lowest priority and are provided to a hard disk drive (HDD) 128 (e.g., slowest option) of the local storage system 125.

The priority rules 123 may prioritize certain examination procedure types over other examination procedure types. For example, the priority rules 123 may specify that head CT scan images from an ER/Trauma imaging modality 112 are a highest priority that are provided to cache memory (e.g., fastest option) of a particular ER workstation 130 to expedite retrieval and review of the medical images. The priority rules 123 may specify that mammogram screening images from an imaging modality corresponding with a scheduled or ordered imaging examination 114 have a second highest priority and are provided to a fast solid state drive (SSD) 126 (e.g., second fastest option) of the local storage system 125. The priority rules 123 may specify that diagnostic mammogram images from an imaging modality corresponding with a scheduled or ordered imaging examination 114 have a third highest priority and are provided to a SSD 127 (e.g., third fastest option) of the local storage system 125. The priority rules 123 may specify that computed radiography or X-ray images from an external source 116 are associated with a lowest priority and are provided to a hard disk drive (HDD) 128 (e.g., slowest option) of the local storage system 125.

The priority rules 123 may prioritize certain image types over other image types. For example, the priority rules 123 may specify that 3D images are prioritized to undergo 3D reconstruction at an image processor 124 of the PACS 120 prior to storing the processed images at an appropriate location, such as a workstation cache 134 or a fast SSD 126, SSD 127, or HDD 128 of a local storage system 125. Although several examples of priority rules 123 are provided, the priority rules may be defined by a user and/or artificial intelligence to prioritize the images based on any suitable image information or combination of different image information. The smart image cache 122 may be configured to determine the image information by parsing the contents of the images received via the ingestion device 121.

The smart image cache engine 122 may comprises suitable logic, circuitry, interfaces and/or code that may be operable to evaluate user interaction with medical images to dynamically update (i.e., add, remove, and/or revise) priority rules 123 stored at a data storage medium of the PACS 120. The smart image cache engine 122 may receive user interaction information from one or more workstations 130. The user interaction information may include image retrieval requests and image processing requests, among other things. In this regard, the smart image cache engine 122 may include, for example, artificial intelligence pattern recognition algorithms and/or machine learning processing functionality configured to detect user interaction patterns and update priority rules 123 to anticipate examination needs. Additionally and/or alternatively, the artificial intelligence pattern recognition techniques or machine learning processing functionality configured to dynamically update priority rules 123 may be provided by a different processor or distributed across multiple processors at the PACS 120 and/or a remote processor communicatively coupled to the PACS 120. For example, the pattern recognition functionality may be provided as a deep neural network that may be made up of, for example, an input layer, an output layer, and one or more hidden layers in between the input and output layers. Each of the layers may be made up of a plurality of processing nodes that may be referred to as neurons. For example, the pattern recognition functionality may include an input layer having a neuron for each user interaction type. The output layer may have a neuron corresponding to a plurality of priority rules. Each neuron of each layer may perform a processing function and pass the processed image interaction information to one of a plurality of neurons of a downstream layer for further processing. As an example, neurons of a first layer may learn to recognize patterns regarding the image processing requests from different image types. The neurons of a second layer may learn to recognize patterns regarding the timing of image retrieval requests from different image sources. The neurons of a third layer may learn recognize patterns of image retrieval requests from different examination procedures based on the detected timing patterns from the second layer. The processing performed by the deep neural network may provide updated priority rules that predict examination needs with a high degree of probability.

The image processor 124 may be one or more central processing units, microprocessors, microcontrollers, servers, and/or the like. The image processor 124 may be an integrated component, or may be distributed across various locations, for example. The image processor 124 may be capable of executing software applications, receiving input information from workstation(s) 130, and generating an output for display at workstation(s) 130 and/or storage at workstation cache 134 or local storage system 125, among other things. The image processor 124 may be capable of executing any set(s) of image processing instructions. For example, the image processor 124 may receive medical images from smart image cache engine 122 and/or workstation(s) 130 and perform 3D reconstruction and/or other post processing algorithms on the received medical images in response to instructions received from the smart image cache engine 122 and/or workstation(s) 130.

Local storage system 125 may comprise a plurality of data storage media having various access speeds. The local storage system 125 may include fast SSD 126, SSD 127, HDD 128, and/or any suitable data storage media. For example, the local storage system 125 may include fast SSD 126 having a fastest access speed, SSD 127 having a second fastest access speed, and HDD 128 having a third fastest access speed. The local storage system 125 may comprise multiple of one or more of the fast SSD 126, SSD 127, and/or HDD 128. The local storage system 125 may additionally and/or alternatively include additional data storage media, such as a low rotations per minute (RPM) HDD having a fourth fastest access speed and/or a tape or optical drive having a slowest access speed. The local storage system 125 may be configured to store medical images received from smart image cache engine 122 for subsequent retrieval by workstation(s) 130.

Communication between image sources 110 and PACS 120 and/or between components of the PACS 120 can be via any one or more types of known networks including a local area network ("LAN"), a wide area network ("WAN"), an intranet, or a global network (for example, Internet). Any two of the components of PACS 120 and/or image sources 110 can be coupled to one another through multiple networks (for example, intranet and Internet) so that not all components of system 100 are required to be coupled to one another through the same network. Any image source 110 and/or component of the PACS 120 can be connected to a network or one another in a wired or wireless fashion.

Still referring to FIG. 1, one or more workstations 130 can be in communication with the smart image cache engine 122, image processor 124, and/or at least one other workstation 130. Workstations 130 can be directly attached to the smart image cache engine 122 and/or communicate with smart image cache engine 122 via one or more networks. Workstations 130 can be located in a single physical location or in a plurality of locations. For example, as shown in FIG. 1, the workstations 130 may include one or more emergency room workstations, one or more mammogram workstations, and/or one or more reading room workstations. In various embodiments, one or more of the workstations 130 may be remote workstations. Workstations 130 can be connected to and communicate via the one or more networks by any suitable combination of wired or wireless data communication links. Each workstation 130 can be implemented using a specialized or general-purpose computer executing a computer program for requesting, viewing, manipulating, and/or storing medical images. Workstations 130 can be personal computers or host attached terminals, for example. Workstations 130 may be any of, for example, a desktop computer, a laptop computer, a notebook computer, a netbook computer, a tablet computer, a mobile phone, or any other electronic device having capabilities suitable for accessing the network.

In various embodiments, the workstation(s) 130 includes a processor 132, storage medium 134, input device(s) 136, and output device(s) 138, among other things. Components of the workstation(s) 130 may be implemented in software, hardware, firmware, and/or the like. The various components of the workstation(s) 130 may be communicatively linked. Components of the workstation(s) 130 may be implemented separately and/or integrated in various forms. For example, an output device 138, such as a display, and input device(s) 136 may be integrated as a touchscreen display.

The input device(s) 136 may include any device(s) capable of communicating information from a user and/or at the direction of the user to the processor 132 of the workstation 130, for example. The input device(s) 136 may include button(s), a touchscreen, motion tracking, voice recognition, a mousing device, keyboard, stylus, camera and/or any other device capable of receiving a user directive. In certain embodiments, one or more of the input devices 136 may be integrated into other components, such as a display output device 138, for example. As an example, input device 136 may include a touchscreen display.

The output device 138 may be any device capable of communicating information to a user. For example, the output device 138 may be a display, printer, and/or speaker, among other things. A display output device 138 may include a liquid crystal display, a light emitting diode display, and/or any suitable display. The display output device 138 can be operable to display information, such as medical images received or retrieved from cache memory 134, smart image cache engine 122, local storage system 125, image processor 124, and/or the like.

The processor 132 may be one or more central processing units, microprocessors, microcontrollers, and/or the like. The processor 132 may be an integrated component, or may be distributed across various locations, for example. The processor 132 may be capable of executing software applications, receiving input information from user input device(s) 136, and generating an output displayable by a display output device 138, among other things. In certain embodiments, the processor 132 may execute an image viewer, retrieve medical images stored to workstation cache 134, transmit requests for image retrieval from local storage system 125, and/or transmit requests for processing at image processor 124, for example. In various embodiments, the information provided by the user input device(s) 136 to the processor 132 may be processed by the processor 132 to retrieve medical images from workstation cache 134, request image retrieval from local storage system 125, request image processing by image processor 124, and/or view, manipulate, annotate, and/or request storage of medical images.

Still referring to FIG. 1, the storage medium 134 may be one or more computer-readable memories, for example, such as cache memory (e.g., static random access memory), a hard disk, floppy disk, CD, CD-ROM, DVD, compact storage, flash memory, dynamic random access memory, read-only memory, electrically erasable and programmable read-only memory and/or any suitable memory. The storage medium 134 may include databases, libraries, sets of information, or other storage accessed by and/or incorporated with the processor 132, for example. The storage medium 134 may be able to store data temporarily or permanently, for example. The storage medium 134 may be capable of storing data generated by the processor 132 and/or instructions readable by the processor 132, among other things. The storage medium 134 can be included in workstations 130 or physically remote from workstations 130. For example, storage medium 134 can be accessible by workstations 130 through a wired or wireless network connection. In various embodiments, the storage medium 134 stores one or more sets of instructions for a computer. The set(s) of instructions may include one or more routines capable of being run or performed by workstations 130. The set(s) of instructions can be embodied in one or more software applications or in computer code. In a representative embodiment, the storage medium 134 includes cache memory that may receive and store high priority medical images provided by smart image cache engine 122 to expedite retrieval and review of the medical images at a display device 138 of the workstation 130.

Figure 2:
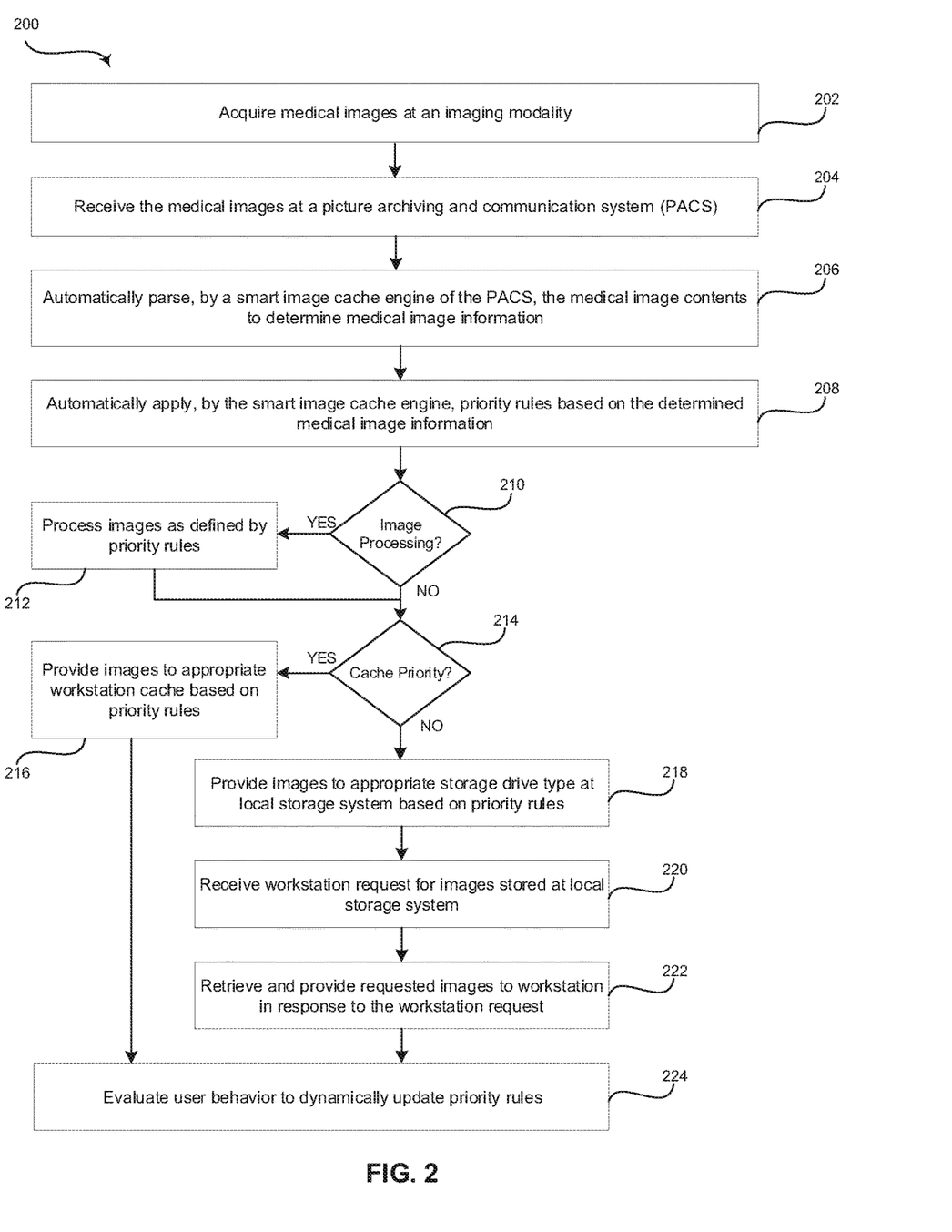
FIG. 2 is a flow chart illustrating exemplary steps that may be utilized for expediting medical image retrieval based on examination priority, in accordance with various embodiments.

FIG. 2 is a flow chart 200 illustrating exemplary steps 202-224 that may be utilized for expediting medical image retrieval based on examination priority, in accordance with various embodiments. Referring to FIG. 2, there is shown a flow chart 200 comprising exemplary steps 202 through 224. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 202, medical images are acquired at an imaging modality 112, 114. For example, the images may be acquired by computed tomography (CT), magnetic resonance imaging (MRI), ultrasound, X-ray, fluoroscopy, angiography, mammography, breast tomosynthesis, positron emission tomography (PET), single photon emission computed tomography (SPECT), endoscopy, microscopy, optical coherence tomography (OCT), and/or an suitable imaging modality. The imaging modality may be provided at a hospital, such as an ER/Trauma imaging modality 112 or a scheduled imaging modality 114. The scheduled imaging modality 114 may be located at an in-patient department, out-patient department, cardiology department, radiology department, obstetrics department, and/or any suitable department of a hospital. The imaging modality may be a remote imaging modality, such as at different hospital or a doctor office, for example.

At step 204, medical images are received at a PACS 120. For example, the medical images acquired at step 202 may be transmitted to an ingestion device 121 of the PACS 120. The ingestion device 121 may be configured to receive the medical images from the imaging modalities 112, 114 and/or third party images 116 and provide the medical images to a smart image cache engine 122 of the PACS 120.

At step 206, a smart image cache engine 122 of the PACS 120 may automatically parse the contents of the medical images to determine medical image information. For example, the smart image cache engine 122 may parse the medical image contents to determine an image source 110 location or type, an imaging modality type, an image type, an examination procedure description, and/or any suitable medical image information. The image source location or type information may be, for example, images from an ER/Trauma imaging modality 112, images from a scheduled or ordered imaging examination 114, or images from an external or third party source 116, among other things. The imaging modality type may be, for example, ultrasound, CT, MRI, CR, X-ray, PET, or the like. The image type may be, for example, 2D, 3D, 4D, or any suitable image type. The examination procedure description may be, for example, a mammogram screening, diagnostic mammogram, head scan, chest scan, broken arm, or any suitable examination procedure description.

At step 208, the smart image cache engine 122 may automatically apply priority rules 123 based on the determined medical image information. For example, the smart image cache engine 122 may apply the priority rules 123 to route the image data to an appropriate storage and/or processing location. For example, the priority rules 123 may prioritize images based on image source 110 locations, examination procedure types, image types, and/or any suitable image information or combination of information parsed from the medical image contents at step 206. The priority rules 123 may be provided as a look-up table (LUT) or as any suitable set of rules. The priority rules 123 may be user-defined and/or dynamically updated based on artificial intelligence detected patterns of user interactions with the medical images.

At step 210, the smart image cache engine 122 may determine whether the priority rules 123 specify that image processing should be performed on the medical images. For example, the priority rules 123 may specify that specific image types, images from particular examination procedure types, images from particular imaging modalities, and/or combinations thereof undergo image processing prior to storage. As an example, 3D images may be prioritized to undergo 3D reconstruction at an image processor 124 of the PACS 120 prior to storing the processed images at an appropriate location based on the priority rules 123.

At step 212, if the smart image cache engine 122 determines image processing should be performed, an image processor 124 of the PACS 120 may process the medical images as defined by the priority rules 123. For example, 3D images may be provided to and post-processed by the image processor 124 according to the priority rules 123 as determined at step 210.

At step 214, the smart image cache engine 122 determines whether the priority rules 123 specify that the medical images should be stored at cache memory 134 of a workstation 130. For example, the priority rules 123 may specify that medical images from an ER or trauma center imaging modality 112 are given a highest priority (e.g., STAT). The priority rules 123 may be user-customizable based on the needs of the system 100. The priority rules 123 may additionally and/or alternatively be customizable based on the needs of the system 100 as detected by artificial intelligence.

At step 216, the smart image cache engine 122 provides the medical images to an appropriate workstation cache 134 based on the priority rules 134 if the smart image cache engine 122 determines the medical images should be stored at cache memory 134 of a workstation 130. For example, the smart image cache engine 122 may store the medical images at a particular workstation 130 in an ER unit or trauma center as defined by the priority rules 123 based on the priority rule determination performed at step 214. The high priority medical images may be provided to cache memory 134 of a specific workstation 130 based on the priority rules 123 such that the medical images can be retrieved at that workstation 130 on an expedited basis. In some cases, the expedited retrieval of medical images from cache memory 134 may reduce the time to display the images at a display device 138 of the workstation 130 by several minutes, which may be critical in emergency situations typical of the ER and trauma center.

At step 218, the smart image cache engine 122 provides the medical images to an appropriate storage drive 126, 127, 128 at a local storage system 125 if the smart image cache engine 122 determines the medical images should not be stored at cache memory 134 of a workstation 130. For example, the smart image cache engine 122 may store medical images at one of a plurality of storage drives 126, 127, 128 as defined by the priority rules 123. The storage drives 126, 127, 128 may include drives having different access speeds, such as a fast SSD 126, an SSD 127, and a HDD 128. Medical images having a higher priority as defined by the priority rules, such as examination procedure types when a radiologist, cardiologist, or the like is reviewing the medical images for a waiting patient (e.g., mammogram screening) may be stored at drives having quicker access times (e.g., fast SSD 126). In contrast, medical images received from third party image sources 116 (e.g., X-ray of broken bones received from doctor office) may be stored at drives having slower access times (e.g., HDD 128). Medical images provided by on-site imaging modalities 114 for non-waiting patients or less urgent review (e.g., a diagnostic mammogram or chest CT scan) may be stored at drives having intermediate access times (e.g., SSD 127). The priority rules 123 may be user-customizable based on the needs of the system 100. The priority rules 123 may additionally and/or alternatively be customizable based on the needs of the system 100 as detected by artificial intelligence.

At step 220, the smart image cache engine 122 may receive a request from a workstation 130 to retrieve medical images stored at the local storage system 125. For example, a reviewing cardiologist or radiologist may request retrieval of medical images from the local storage system 125 via a user input device 136 of the workstation 130.

At step 222, the smart image cache engine 122 may retrieve and provide the requested medical images to the workstation 130 in response to the workstation request. For example, the smart image cache engine 122 may receive the request from the workstation 130 and in response, retrieve the requested medical images from the appropriate drive 126, 127, 128 of the local storage system 125. The retrieved medical images may be provided by the smart image cache engine 122 to the requesting workstation 130 for presentation at a display device 138 of the workstation 130.

At step 224, artificial intelligence may evaluate user behavior to dynamically update the priority rules 123. For example, the smart image cache engine 122 may evaluate user interaction with medical images to dynamically add, remove, and/or revise (i.e., update) priority rules 123 stored at a data storage medium of the PACS 120. The smart image cache engine 122 may receive user interaction information, such as image retrieval requests, image processing requests, and the like from one or more workstations 130. The smart image cache engine 122 may include, for example, artificial intelligence pattern recognition algorithms and/or machine learning processing functionality configured to analyze the received user interaction information to detect patterns. The artificial intelligence of the smart image cache engine 122 may update priority rules 123 to anticipate examination needs based on the detected patterns. As an example, if a pattern is detected of receiving requests for retrieving medical images associated with a specific examination procedure type for immediate review at a particular workstation, the artificial intelligence of the smart image cache engine 122 may revise an existing rule or create a new rule in the priority rules 123 assigning a highest priority to the medical images having the specific examination procedure type such that the medical images are provided to the cache memory 134 of the particular workstation 130. As another example, if the artificial intelligence of the smart image cache engine 122 detects a pattern of requests from workstations 130 for post-processing of a specific image type, imaging modality type, and/or examination procedure type, the artificial intelligence of the smart image cache engine 122 may update the priority rules 123 to automatically provide the image processor 124 with those medical images for post-processing prior to storage at the local storage system 125.

Aspects of the present disclosure provide a method 200 and system 100 for expediting medical image retrieval based on examination priority. In accordance with various embodiments, the method 200 may comprise receiving 204, by at least one processor 122 of a picture archiving and communication system (PACS) 120, medical images provided by one of a plurality of image sources 110. The method 200 may comprise automatically parsing 206, by the at least one processor 122, contents of the medical images to determine medical image information. The method 200 may comprise automatically applying 208, by the at least one processor 122, priority rules 123 based on the determined medical image information. The priority rules 123 may specify one of a plurality of image storage locations 126, 127, 128, 134 for storing the medical images. At least one of the plurality of image storage locations 126, 127, 128, 134 may be a workstation cache memory 134. At least two of the plurality of image storage locations 126, 127, 128, 134 may be drives 126, 127, 128 of a local storage system 125 of the PACS 120. Each of the at least two of the plurality of image storage locations 126, 127, 128, 134 may have different image access speeds that are slower than an access speed of the workstation cache memory 134. The method 200 may comprise storing 216, 218, by the at least one processor 122, the medical images at the specified one of the plurality of image storage locations 126, 127, 128, 134 as defined by the priority rules 123. The method 200 may comprise retrieving 222 the medical images from the specified one of the plurality of image storage locations 126, 127, 128, 134 in response to a request to view the medical images at a workstation 130. The method 200 may comprise presenting 222, at a display device 138 of the workstation 130, the medical images retrieved from the specified one of the plurality of image storage locations 126, 127, 128, 134.

In a representative embodiment, the medical image information may comprise one or more of an image source location or type, an imaging modality type, an image type, or an examination procedure description. In an exemplary embodiment, the priority rules 123 may be arranged as a look-up table. In various embodiments, the drives 126, 127, 128 of the local storage system 125 may comprise a plurality of a fast solid state drive (SSD) 126 having a fast SSD image access speed, a SSD 127 having an SSD image access speed, and a hard disk drive (HDD) 128 having a HDD image access speed. The HDD image access speed may be slower than the SSD image access speed. The SSD image access speed may be slower than the fast SSD image access speed. In certain embodiments, the method 200 may comprise determining 210, by the at least one processor 122, to perform image post-processing on the medical images based on the priority rules 123. The method 200 may comprise performing 212, by at least one image processor 124, the image post-processing on the medical images as defined by the priority rules 123 prior to the storing 216, 218 the medical images at the specified one of the plurality of image storage locations 126, 127, 128, 134. In a representative embodiment, the method 200 may comprise evaluating 224, by artificial intelligence executed by the at least one processor 122, user interaction with the medical images to detect patterns of medical image use. The method 200 may comprise updating 222, by the artificial intelligence, the priority rules 123 based on the detected patterns of medical image use. In an exemplary embodiment, the user interaction with the medical images may comprise one or both of image retrieval requests and image processing requests. The updating the priority rules 123 may comprise one or more of adding a new priority rule, removing an existing priority rule, or revising one or more of the priority rules 123.

Various embodiments provide a system 100 for expediting medical image retrieval based on examination priority. The system 100 may comprise a picture archiving and communication system (PACS) 120 comprising a plurality of image storage locations 126, 127, 128, 134, at least one processor 122, and a workstation 130. The plurality of image storage locations 126, 127, 128, 134 may comprise a workstation cache memory 134 and a local storage system 125 comprising at least two drives 126, 127, 128. The at least two drives 126, 127, 128 may have different image access speeds that are slower than an access speed of the workstation cache memory 134. The at least one processor 122 may be configured to receive medical images provided by one of a plurality of image sources 110. The at least one processor 122 may be configured to automatically parse contents of the medical images to determine medical image information. The at least one processor 122 may be configured to automatically apply priority rules 123 based on the determined medical image information. The priority rules 123 may specify one of the plurality of image storage locations 126, 127, 128, 134 for storing the medical images. The at least one processor 122 may be configured to store the medical images at the specified one of the plurality of image storage locations 126, 127, 128, 134 as defined by the priority rules 123. The workstation 130 may comprise a display device 138 and the workstation cache memory 134. The workstation 130 may be configured to receive a request to view the medial images at the display device 138. The workstation 130 may be configured to present the medical images retrieved from the specified one of the plurality of image storage locations 126, 127, 128, 134 at the display device 138.

In an exemplary embodiment, the medical image information may comprise one or more of an image source location or type, an imaging modality type, an image type, or an examination procedure description. In various embodiments, the at least two drives 126, 127, 128 of the local storage system may comprise a plurality of a fast solid state drive (SSD) 126 having a fast SSD image access speed, a SSD 127 having an SSD image access speed, and a hard disk drive (HDD) 128 having a HDD image access speed. The HDD image access speed may be slower than the SSD image access speed. The SSD image access speed may be slower than the fast SSD image access speed. In certain embodiments, the at least one processor 122 may be configured to determine to perform image post-processing on the medical images based on the priority rules 123. The at least one processor 124 may be configured to perform the image post-processing on the medical images as defined by the priority rules 123 prior to the storing the medical images at the specified one of the plurality of image storage locations 126, 127, 128, 134. In a representative embodiment, the at least one processor 122 may comprise artificial intelligence configured to evaluate user interaction with the medical images to detect patterns of medical image use. The at least one processor 122 may update the priority rules 123 based on the detected patterns of medical image use. In an exemplary embodiment, the user interaction with the medical images may comprise one or both of image retrieval requests and image processing requests. The update of the priority rules 123 may comprise one or more of adding a new priority rule, removing an existing priority rule, or revising one or more of the priority rules 123.

Certain embodiments provide a non-transitory computer readable medium having stored thereon, a computer program having at least one code section. The at least one code section is executable by a machine for causing the machine to perform steps 200. The steps 200 may comprise automatically parsing 206 contents of medical images to determine medical image information. The medical images may be received from one of a plurality of image sources 110 at a picture archiving and communication system (PACS) 120. The steps 200 may comprise automatically applying 208 priority rules 123 based on the determined medical image information. The priority rules 123 may specify one of a plurality of image storage locations 126, 127, 128, 134 for storing the medical images. At least one of the plurality of image storage locations 126, 127, 128, 134 may be a workstation cache memory 134. At least two of the plurality of image storage locations 126, 127, 128, 134 may be drives 126, 127, 128 of a local storage system 125 of the PACS 120. Each of the at least two of the plurality of image storage locations 126, 127, 128 may have different image access speeds that are slower than an access speed of the workstation cache memory 134. The steps 200 may comprise storing 216, 218 the medical images at the specified one of the plurality of image storage locations 126, 127, 128, 134 as defined by the priority rules 123. The steps 200 may comprise retrieving 216, 222 the medical images for presentation at a display device 138 of a workstation 130. The medical images may be retrieved from the specified one of the plurality of image storage locations 126, 127, 128, 134 in response to a request 220 to view the medical images at the workstation 130.

In various embodiments, the medical image information may comprise one or more of an image source location or type, an imaging modality type, an image type, or an examination procedure description. In certain embodiments, the priority rules 123 may be arranged as a look-up table. In a representative embodiment, the drives 126, 127, 128 of the local storage system 125 may comprise a plurality of a fast solid state drive (SSD) 126 having a fast SSD image access speed, a SSD 127 having an SSD image access speed, and a hard disk drive (HDD) 128 having a HDD image access speed. The HDD image access speed may be slower than the SSD image access speed. The SSD image access speed may be slower than the fast SSD image access speed. In an exemplary embodiment, the steps 200 may comprise determining 210 to perform image post-processing on the medical images based on the priority rules 123. The steps 200 may comprise performing 212 the image post-processing on the medical images as defined by the priority rules 123 prior to the storing 216, 218 the medical images at the specified one of the plurality of image storage locations 126, 127, 128, 134. In various embodiments, the steps 200 may comprise evaluating 224, by artificial intelligence, user interaction with the medical images to detect patterns of medical image use. The steps 200 may comprise updating 224, by the artificial intelligence, the priority rules 123 based on the detected patterns of medical image use. In certain embodiments, the user interaction with the medical images may comprise one or both of image retrieval requests and image processing requests. The updating 224 the priority rules 123 may comprise one or more of adding a new priority rule, removing an existing priority rule, or revising one or more of the priority rules 123.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for expediting medical image retrieval based on examination priority.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
    receiving, by at least one processor of a picture archiving and communication system (PACS), medical images provided by one of a plurality of image sources;
    automatically parsing, by the at least one processor, contents of the medical images to determine medical image information;
    evaluating, by artificial intelligence executed by the at least one processor, user interaction with the medical images to detect patterns of medical image use; and
    updating, by the artificial intelligence, the priority rules based on the detected patterns of medical image use;
    wherein the user interaction with the medical images comprises one or both of image retrieval requests and image processing requests, and the updating the priority rules comprises one or more of adding a new priority rule, removing an existing priority rule, or revising one or more of the priority rules;

automatically applying, by the at least one processor, priority rules based on the determined medical image information, the priority rules specifying one of a plurality of image storage locations for storing the medical images, wherein at least one of the plurality of image storage locations is a workstation cache memory, and wherein at least two of the plurality of image storage locations are drives of a local storage system of the PACS, each of the at least two of the plurality of image storage locations having different image access speeds that are slower than an access speed of the workstation cache memory;

storing, by the at least one processor, the medical images at the specified one of the plurality of image storage locations as defined by the priority rules;

retrieving the medical images from the specified one of the plurality of image storage locations in response to a request to view the medical images at a workstation; and presenting, at a display device of the workstation, the medical images retrieved from the specified one of the plurality of image storage locations.

2. The method of claim 1, wherein the medical image information comprises one or more of an image source location or type, an imaging modality type, an image type, or an examination procedure description.

3. The method of claim 1, wherein the drives of the local storage system comprises a plurality of:
a fast solid state drive (SSD) having a fast SSD image access speed,
a SSD having an SSD image access speed, and
a hard disk drive (HDD) having a HDD image access speed,
wherein the HDD image access speed is slower than the SSD image access speed and the SSD image access speed is slower than the fast SSD image access speed.

4. The method of claim 1, comprising:
determining, by the at least one processor, to perform image post-processing on the medical images based on the priority rules; and
performing, by at least one image processor, the image post-processing on the medical images as defined by the priority rules prior to the storing the medical images at the specified one of the plurality of image storage locations.

5. A picture archiving and communication system (PACS) comprising:
a plurality of image storage locations comprising:
a workstation cache memory; and
a local storage system comprising at least two drives, the at least two drives having different image access speeds that are slower than an access speed of the workstation cache memory;
at least one processor configured to:
receive medical images provided by one of a plurality of image sources;
automatically parse contents of the medical images to determine medical image information;
evaluate user interaction with the medical images to detect patterns of medical image use; and update the priority rules based on the detected patterns of medical image use; and wherein the user interaction with the medical images comprises one or both of image retrieval requests and image processing requests, and the update of the priority rules comprises one or more of adding a new priority rule, removing an existing priority rule, or revising one or more of the priority rules;
automatically apply priority rules based on the determined medical image information, the priority rules specifying one of the plurality of image storage locations for storing the medical images; and
store the medical images at the specified one of the plurality of image storage locations as defined by the priority rules; and
a workstation comprising a display device and the workstation cache memory, the workstation configured to:
receive a request to view the medial images at the display device; and
present the medical images retrieved from the specified one of the plurality of image storage locations at the display device.

6. The system of claim 5, wherein the medical image information comprises one or more of an image source location or type, an imaging modality type, an image type, or an examination procedure description.

7. The system of claim 5, wherein the at least two drives of the local storage system comprises a plurality of:
a fast solid state drive (SSD) having a fast SSD image access speed,
a SSD having an SSD image access speed, and
a hard disk drive (HDD) having a HDD image access speed,
wherein the HDD image access speed is slower than the SSD image access speed and the SSD image access speed is slower than the fast SSD image access speed.

8. The system of claim 5, wherein the at least one processor is configured to:
determine to perform image post-processing on the medical images based on the priority rules; and
perform the image post-processing on the medical images as defined by the priority rules prior to the storing the medical images at the specified one of the plurality of image storage locations.

9. A non-transitory computer readable medium having stored thereon, a computer program having at least one code section, the at least one code section being executable by a machine for causing the machine to perform steps comprising:
automatically parsing contents of medical images to determine medical image information, the medical images received from one of a plurality of image sources at a picture archiving and communication system (PACS);
evaluating, by artificial intelligence, user interaction with the medical images to detect patterns of medical image use; and updating, by the artificial intelligence, the priority rules based on the detected patterns of medical image use, and wherein the user interaction with the medical images comprises one or both of image retrieval requests and image processing requests, and the updating the priority rules comprises one or more of adding a new priority rule, removing an existing priority rule, or revising one or more of the priority rules;
automatically applying priority rules based on the determined medical image information, the priority rules specifying one of a plurality of image storage locations for storing the medical images, wherein at least one of the plurality of image storage locations is a workstation cache memory, and wherein at least two of the plurality of image storage locations are drives of a local storage system of the PACS, each of the at least two of the plurality of image storage locations having different image access speeds that are slower than an access speed of the workstation cache memory;

storing the medical images at the specified one of the plurality of image storage locations as defined by the priority rules; and retrieving the medical images for presentation at a display device of a workstation, the medical images retrieved from the specified one of the plurality of image storage locations in response to a request to view the medical images at the workstation.

10. The non-transitory computer readable medium of claim 9, wherein the medical image information comprises one or more of an image source location or type, an imaging modality type, an image type, or an examination procedure description.

11. The non-transitory computer readable medium of claim 9, wherein the drives of the local storage system comprises a plurality of:

a fast solid state drive (SSD) having a fast SSD image access speed, a SSD having an SSD image access speed, and a hard disk drive (HDD) having a HDD image access speed, wherein the HDD image access speed is slower than the SSD image access speed and the SSD image access speed is slower than the fast SSD image access speed.

12. The non-transitory computer readable medium of claim 9, comprising:

determining to perform image post-processing on the medical images based on the priority rules; and performing the image post-processing on the medical images as defined by the priority rules prior to the storing the medical images at the specified one of the plurality of image storage locations.

* * * * *